US009681941B2

(12) United States Patent
Griffin et al.

(10) Patent No.: US 9,681,941 B2
(45) Date of Patent: Jun. 20, 2017

(54) ENDOTINE BREAST RECONSTRUCTION DEVICE AND METHODS

(71) Applicant: MicroAire Surgical Instruments, LLC, Charlottesville, VA (US)

(72) Inventors: Robert Griffin, Charlottesville, VA (US); Mark A. Brzezienski, Ooltewah, TN (US); Devan Griner, Ooltewah, TN (US)

(73) Assignee: MicroAire Surgical Instruments, Charlottesville, VA (US)

( * ) Notice: Subject to any disclaimer, the term of this patent is extended or adjusted under 35 U.S.C. 154(b) by 91 days.

(21) Appl. No.: 14/670,904

(22) Filed: Mar. 27, 2015

(65) Prior Publication Data

US 2015/0272724 A1 Oct. 1, 2015

Related U.S. Application Data

(60) Provisional application No. 61/972,076, filed on Mar. 28, 2014.

(51) Int. Cl.
*A61F 2/12* (2006.01)
*A61F 2/00* (2006.01)

(52) U.S. Cl.
CPC .............. *A61F 2/12* (2013.01); *A61F 2/0063* (2013.01); *A61F 2220/0016* (2013.01)

(58) Field of Classification Search
CPC ........................................................ A61F 2/12
See application file for complete search history.

(56) References Cited

U.S. PATENT DOCUMENTS

| | | | |
|---|---|---|---|
| 6,645,226 B1 | 11/2003 | Jacobs et al. | |
| 7,056,331 B2 | 6/2006 | Kaplan et al. | |
| 7,857,829 B2 | 12/2010 | Kaplan et al. | |
| 7,976,519 B2 | 7/2011 | Bubb et al. | |
| 2007/0021779 A1 | 1/2007 | Garvin et al. | |
| 2007/0156175 A1 | 7/2007 | Weadock et al. | |
| 2008/0208251 A1 | 8/2008 | Weadock et al. | |
| 2010/0137679 A1* | 6/2010 | Lashinski | A61B 17/0401 600/37 |
| 2012/0143329 A1* | 6/2012 | Kim | A61F 2/12 623/8 |
| 2014/0081397 A1 | 3/2014 | Kalus | |
| 2014/0276993 A1 | 9/2014 | Reilly et al. | |

* cited by examiner

*Primary Examiner* — Thomas J Sweet
*Assistant Examiner* — Daniel Bissing
(74) *Attorney, Agent, or Firm* — Whitham, Curtis & Cook (57) ABSTRACT

Methods and devices are disclosed for breast reconstruction surgery. An implantable fixation device is attached to pectoralis muscle tissue and a tissue graft that forms a sling for supporting a tissue expander or permanent breast implant. The implantable fixation device provides flap stabilization of overlying skin and reduces breast reconstruction complications such as seroma formation.

5 Claims, 13 Drawing Sheets

ENDOTINE BREAST RECONSTRUCTION DEVICE AND METHODS

CROSS-REFERENCE TO RELATED APPLICATION

This application claims the priority of U.S. Provisional Patent Application No. 61/972,076, filed Mar. 28, 2014, the complete contents of which are herein incorporated by reference.

FIELD OF THE INVENTION

This invention generally relates to breast reconstruction surgery and, more particularly, devices and methods for tissue flap stabilization.

BACKGROUND

One approach to breast reconstruction is the harvesting of autologous tissue from other sites on the patient's own body for use in place of removed breast tissue. This can include but is not limited to the following tissue extractions known in the art: latissimus dorsi flap, transverse rectus abdominus myocutaneous (TRAM) flap, deep inferior epigastric artery perforator (DIEP) flap, latissimus dorsi myocutaneous (LDM) flap, and superior gluteal artery perforator (SGAP) flap. There are significant drawbacks to the use of autologous tissue grafts, in particular the requirement for healing at the secondary location from which tissue is taken.

Approximately 70-80% of all breast reconstructions performed in the United States utilize a technique referred to as a "skin sparing mastectomy" where the initial cancer surgery and breast reconstruction are performed in a single procedure. Specially treated cadaveric, bovine, and porcine tissues including acellular dermis, acellular pericardium, and/or acellular porcine dermis are used to create a tissue sling between the inferior border of the pectoralis muscle and the inframammary fold. The combination of tissue sling and pectoralis muscle provides a pocket in which a tissue expander is placed to facilitate expansion of the pocket for future placement of a permanent breast implant 3-6 months in the future after healing has occurred.

Although this is the dominant reconstruction technique for breast cancer, it has several well documented complications. The most documented is seroma formation. Seroma is a fluid accumulation within the surgical site that if left unattended can lead to infections and possible loss of the implanted tissue expander. There is a wide range in severity of seromas, with some easily treated by the surgeon through needle aspiration and others requiring surgical debridement and closure.

It is the current opinion of most plastic surgeons that the very smooth acellular tissues of the tissue sling allow the subcutaneous tissues to slide or easily move during the early part of the patient's recovery. As with skin grafts, tissue movement slows the healing process. With this type of breast reconstruction procedure, tissue flap movement above the tissue sling not only retards healing but can exacerbate fluid accumulation and seroma formation.

U.S. Patent App. Pub. No. 2014/0081397 discloses breast reconstruction procedures aimed at selecting a breast implant size that avoids excessive tension in surrounding tissue and proper breast implant position and symmetry. An acellular dermal matrix is sutured to the chest wall under the pectoralis muscle to provide a hammock for a breast implant. While the procedures offer insights into optimization of implant sizing, no attention is given to manner in which the incisions are closed let alone stabilization of the skin flap. Thus, the disclosed procedures are susceptible to the same post-operative complications (e.g., seroma formation) of other skin sparing mastectomy techniques.

U.S. Patent App. Pub. No. 2014/0276993 discloses an absorbable synthetic braided matrix for breast reconstruction and hernia repair. For breast reconstruction, the matrix may serve as an internal hammock or sling to support a tissue expander, breast implant, or breast tissue. In essence, the matrix may be used instead of biological slings prepared from, for example, porcine or bovine tissue. A drawback to this device is insufficient stabilization of the tissue flap relative to the matrix. Problems such as seroma formation may arise similar to the case of using acellular tissue slings. Another disadvantage of this device is that it is designed to degrade after a period of six to twelve months after implantation. After such time, support of a tissue expander or breast implant must be supplied by the patient's cellular ingrowth into the matrix. As such, the implant itself provides no guarantee of long term support.

U.S. Patent App. Pub. No. 2007/0021779 discloses surgical fasteners having two halves which pull together in a manner akin to a cable tie. Each half is imbedded in the opposite side of a wound or laceration. As the two halves are pulled together, the opposing sides of the wound are likewise pulled together, closing the opening. A limitation of the surgical fasteners is their application to tissue approximation of a single tissue layer. They fail to provide stabilization between adjacent layers and permit sliding between the layer in which the fastener is imbedded and adjacent tissue layers or structures.

U.S. Patent App. Pub. Nos. 2007/0156175 and 2008/0208251 disclose devices for attaching, relocating, and reinforcing tissue. In an embodiment, two support plates with angled barbs are connected to one another via suture or a mesh material. As in 2007/0021779, discussed above, the two ends may be brought together to adjust the distances therebetween. Again, the application is directed to tissue approximation, and no configuration is disclosed which provides flap stabilization in a reconstructed breast.

In the field of breast reconstruction surgery, problems such as seroma formation persist in spite of developments in the fields of wound healing and tissue approximation such as the devices and methods disclosed in the patents and published patent applications discussed above.

SUMMARY

In one aspect of the invention, seroma formation and other complications resulting from breast reconstruction surgery are mitigated or eliminated according to devices and methods which address the underlying problem of tissue layer displacement in the reconstructed breast(s). In particular, devices and methods are disclosed which provide skin flap stabilization in addition to tissue approximation. As used herein, stabilization of the skin flap is defined as the prevention of the skin flap from sliding relative to underlying tissues or structures, in particular an implanted tissue graft or the patient's own tissue (e.g., pectoralis muscle). Moreover, the present invention attends to the particular problems introduced when the implantation of non-autologous soft tissue is used to create a tissue sling. Fixation and stabilization of overlying skin of reconstructed breasts can preferably be provided with respect to acellular dermis, acellular bovine pericadium, porcine acellular dermis, and/or cadaveric tissue grafts.

According to an exemplary method, skin flap stabilization in breast reconstruction surgery is provided by a series of steps which include securing in a breast reconstruction patient a tissue sling configured to support a tissue expander or breast implant. The tissue sling comprises non-autologous soft tissue including one or more of acellular dermis, acellular bovine pericardium, porcine acellular dermis, and a cadaveric tissue graft. Fixation of the implantable fixation device preferably includes using a platform (i.e., backing) fixable with tines and/or suture to both the tissue sling and the pectoralis muscle tissue of the patient. The closure of overlying skin is performed such that outward projecting tines contact or imbed in an undersurface of the overlying skin.

Another aspect of the invention is the determination of specific vectors of lift associated with breast reconstruction. The implantable fixation device(s) are oriented along specific vectors of lift to stabilize one or more of the tissue sling and pectoralis muscle tissue with respect to the ribbon flap of the overlying skin tissue. The implantable fixation device has a platform size, shape, porosity, flexibility, material composition, and suture hole and/or tine configuration such that, after being fixed to both a tissue sling and pectoralis muscle tissue of the patient and a closure of overlying skin such that outward projecting tines of the plurality of tines of the platform contact or imbed in an undersurface of the overlying skin, the implantable fixation device stabilizes the tissue sling with respect to the overlying skin flap. In addition to providing tissue stabilization, implantable fixation devices may furthermore distribute tension from wound closure.

The implantable fixation device may take a variety of configurations. The density, shape, length, and orientation of attachment points on the backing may be varied. The flexibility of the backing is also variable between embodiments and dependent on the materials used and dimensions of the backing. In some exemplary embodiments, the devices are bioabsorbable, and the attachment points uniformly distribute tension over the contact area between the implantable fixation device and tissue.

A wide variety of incisions are used in breast reconstruction. Variations are generally based on initial evaluations of breast symmetry, the degree of ptosis and projection, as well as if axillary dissection of the lymph nodes is required. Based on the incision location, mass of the skin flap, and vectors of stabilization, an implantable fixation device according to the invention may be positioned vertical, oblique, or horizontal. As of the filing of this disclosure, roughly 80% of all breast reconstructions utilize a tissue sling arranged in a horizontal position. Some exemplary embodiments provide implantable fixation devices (e.g., of ribbon geometry) that are arranged in a patient in a horizontal position to stabilize the lateral area of the overlying skin flap. This configuration is well suited for horizontal tissue slings. The lateral area of the overlying skin flap is subject to movement due to gravity and tissue mass when a patient sleeps, rolls over, or raises her arms, along with a variety of daily activities. Horizontal incisions may include a vertically arranged implantable fixation device to stabilize the skin flap below the incision from the effects of gravity pulling downward. The typical zone of overlying tissue flap instability will tend to be the subcutaneous tissue and fat directly above the tissue sling. This zone is the lower pole of the breast.

DETAILED DESCRIPTION

Figure 1:
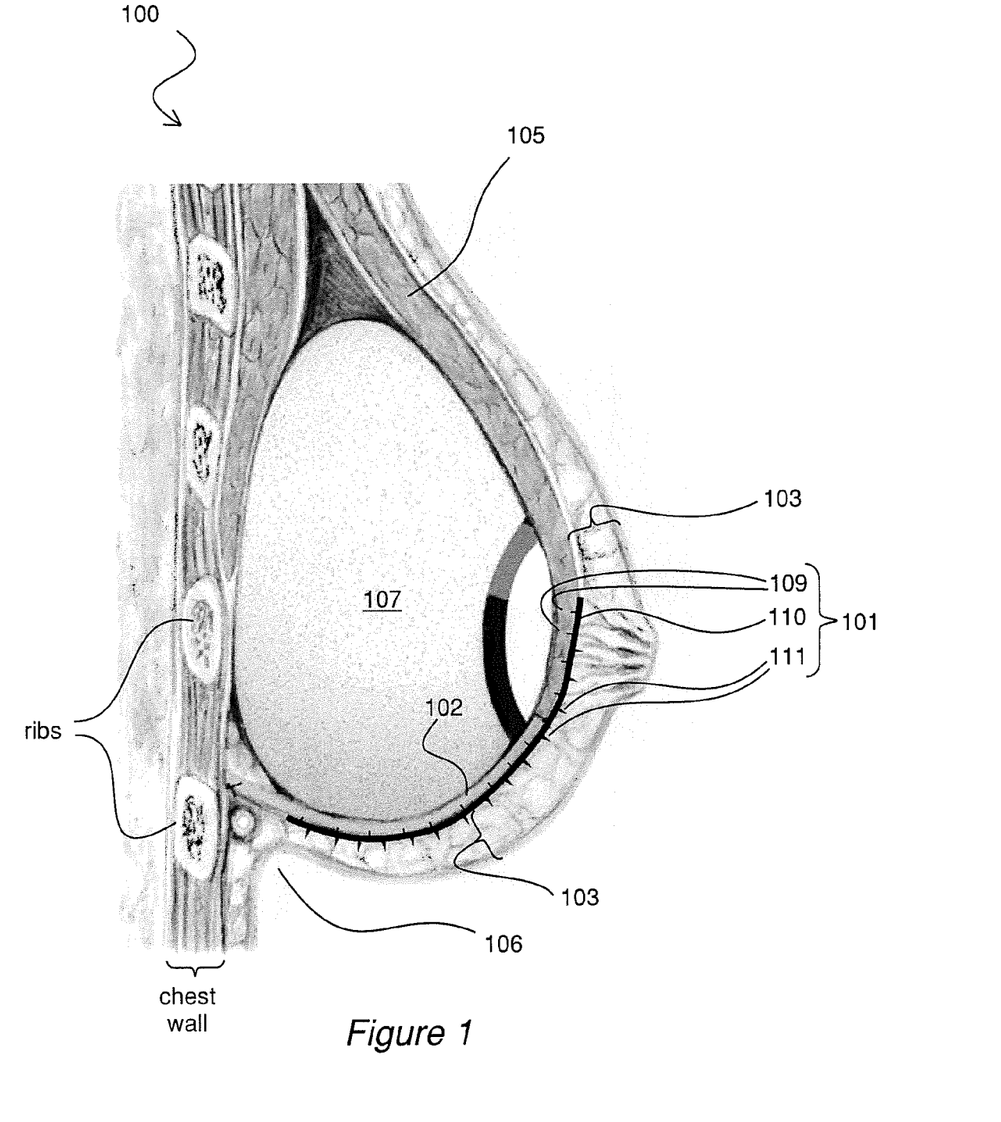
FIG. 1 shows a sectional side view of a breast after breast reconstruction surgery.

Referring now to the drawings, and more particularly FIG. 1, a side cross-sectional view of a reconstructed female human breast 100 is shown in which an implantable fixation device 101 was implanted during the breast reconstruction surgery. After removal of cancerous and other tissues (e.g., nipple areolar complex) in accordance with known mastectomy procedures, breast reconstruction may be performed immediately or as a follow-up surgical procedure. In addition to the implantable fixation device 101, a tissue sling 102 is also secured in the patient.

The tissue sling 102 consists of non-autologous tissue or is a combination of autologous and non-autologous tissues. In particular, the tissue sling 102 may comprise non-autologous soft tissue including one or more of acellular dermis, acellular bovine pericardium, porcine acellular dermis, and a cadaveric tissue graft. Exemplary commercially available tissue grafts suitable for use in the sling 102 in accordance with the invention are Strattice™ Reconstructive Tissue Matrix (a trademark of LifeCell Corporation) and Allo-Derm® Regenerative Tissue Matrix (a registered trademark of LifeCell Corporation). Non-autologous tissue grafts have various advantages over autologous grafts. As one example, no secondary wound site is introduced where autologous tissue would be harvested. A secondary wound site introduces a second set of potential complications, including seroma formation, infection, reduced motor ability (e.g., due to a removal of muscles and/or tendon tissue), scar formation, and negative cosmetic effects. In addition, adequate blood supply must be provisioned for transplanted autologous tissue grafts such as muscle. In some cases the transplant leads to necrosis which can require surgery to remove the dead tissue and reform the breast mound. Furthermore, autologous tissue grafts are unsuited for creation of a sling to support a tissue expander or breast implant. An average sling may be, for example, 2-3 inches wide at its largest width and 10-12 inches in total length. There is no autologous tissue on the human body of this size which can be removed without dramatic injury/complications to the secondary surgical site from which the tissue would be taken.

Figure 2:
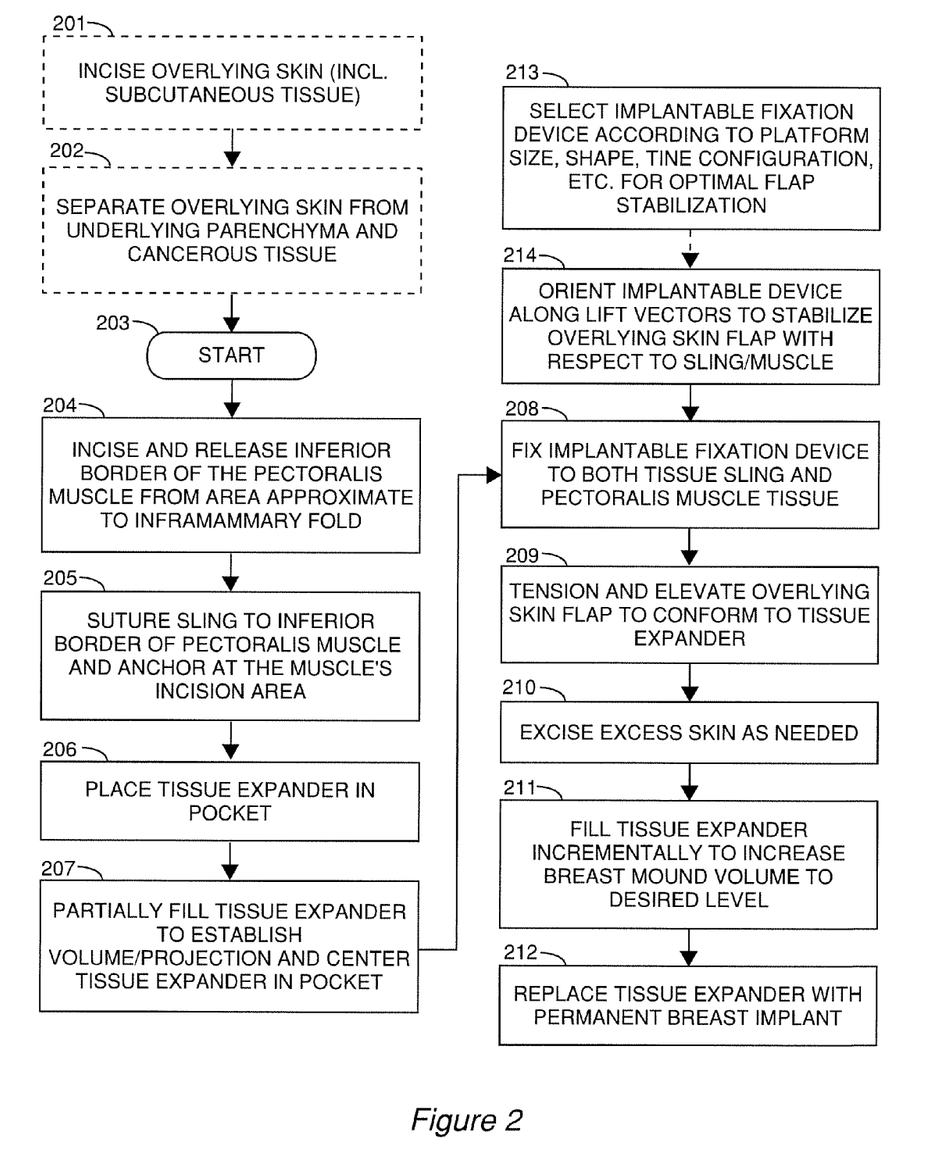
FIG. 2 shows an exemplary surgical procedure for breast reconstructions surgery.

FIG. 2 shows an exemplary surgical procedure for breast reconstruction which will be explained in connection with FIG. 1. At block 201, overlying skin (e.g., dermis, epidermis, and subcutaneous tissues collectively) is incised. Various factors influence the location and orientation of the one or more incisions, including, for example, tumor location and depth as well as the desired shape and appearance of the reconstructed breast. Incisions range from substantially horizontal at an upper part of the breast to vertical incisions, e.g., from an inferior border of the nipple areolar complex down to the inframammary fold. One well known incision pattern is the Wise incision pattern. Most if not all incision patterns used in existing mastectomy procedures are suitable for applications of the present invention. At block 202, the overlying skin is separated from the underlying parenchyma and cancerous tissue. Both blocks 201 and 202 are shown in broken lines to indicate that they are steps of the mastectomy. Once the cancerous breast tissue has been removed, the reconstruction procedure begins at block 203.

The inferior border of the pectoralis muscle 105 is incised and released from an area approximate to the inframammary fold 106 (block 204). The tissue sling 102 is then sutured to the inferior border of the pectoralis muscle 105 and anchored at the muscle's incision area which equates to the level of the inframammary fold 106 (block 205). This configuration allows for a tissue expander 107 that is initially un-inflated to be placed in the resulting pocket at block 206. The tissue expander 107 is partially filled to establish volume and projection and center the tissue expander in the pocket (block 207).

The implantable fixation device 101 is then fixed to both the tissue sling 102 and pectoralis muscle tissue 105 (block 208). Attachment of the implantable fixation device can be accomplished with sutures, tines (i.e., tacks), or a combination of sutures and tines. A plurality of posteriorly projecting tines 109 are shown in the illustrative embodiment of FIG. 1. These tines project from a backing 110 (i.e., platform) which supports and maintains the tines 109 in their collective configuration. With the implantable fixation device 101 stable and attached to both the sling 102 and pectoralis muscle 105, the flap of overlying skin 103 is tensioned and elevated to conform to the tissue expander 107 (block 209). This closure of the overlying skin is such that anteriorly projecting tines 111 contact or imbed in an undersurface of the overlying skin 103. Excess skin, if present, is resected to achieve a smooth closure (block 210). Over the ensuing months post operation, the tissue expander 107 is filled incrementally to increase the breast mound volume to the desired level (e.g, to be symmetric with the other breast) (block 211). Once the desired amount of volume and projection is achieved, the tissue expander 107 is usually deflated, removed, and replaced with a permanent silicone or saline breast implant (block 212). As an alternative, the tissue expander may serve as the permanent implant.

In preferred embodiments, the breast reconstruction procedure of FIG. 2 further includes a step of orienting the implantable fixation device 101 along one or more lift vectors to optimize stabilization of the flap of overlying skin with respect to the tissue sling and/or pectoralis muscle (block 214). Generally, a direction of lift along which the implantable fixation device 101 is oriented should be the direction perpendicular to the closed incision. If the closed incision is curved, the implantable fixation device should be oriented such that the lift vector supplied to the tissue is perpendicular to at least the portion of the closed incision where the implantable fixation device bridges the opposite sides of the incision. Lift vectors vary based on the location (s) of the incisions made in block 201. In addition to the orientation step of block 214, there may also be a selection step in which the implantable fixation device 101 is selected according to a platform size, shape, and tine configuration such that, after the steps of fixing and closing (blocks 208-209), the implantable fixation device provides optimal stabilization to the flap of overlying skin with respect to the tissue sling and pectoralis muscle (block 213).

Figure 3A:
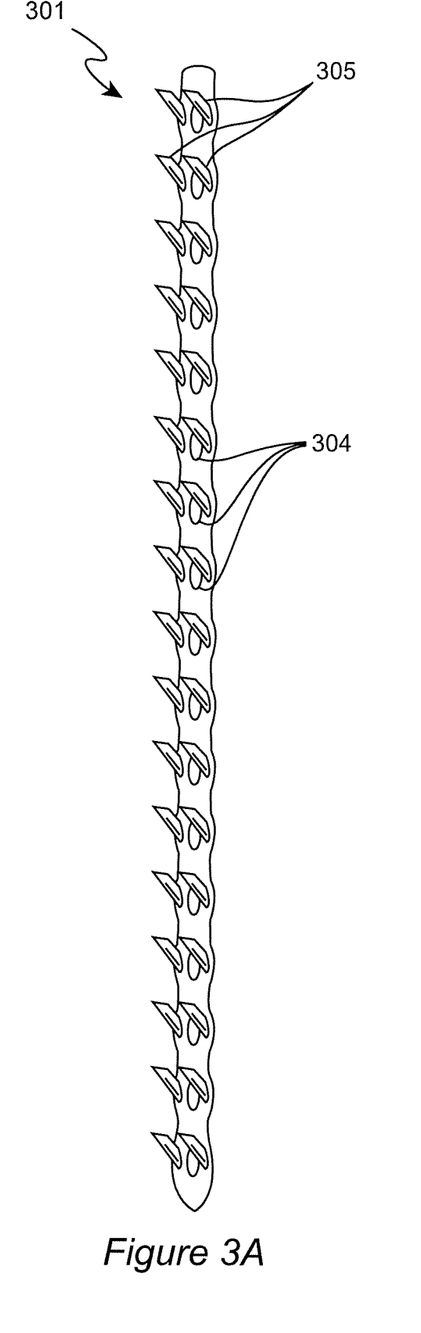
FIGS. 3A and 3B show example implantable fixation devices with a ribbon configuration.
Figure 3B:
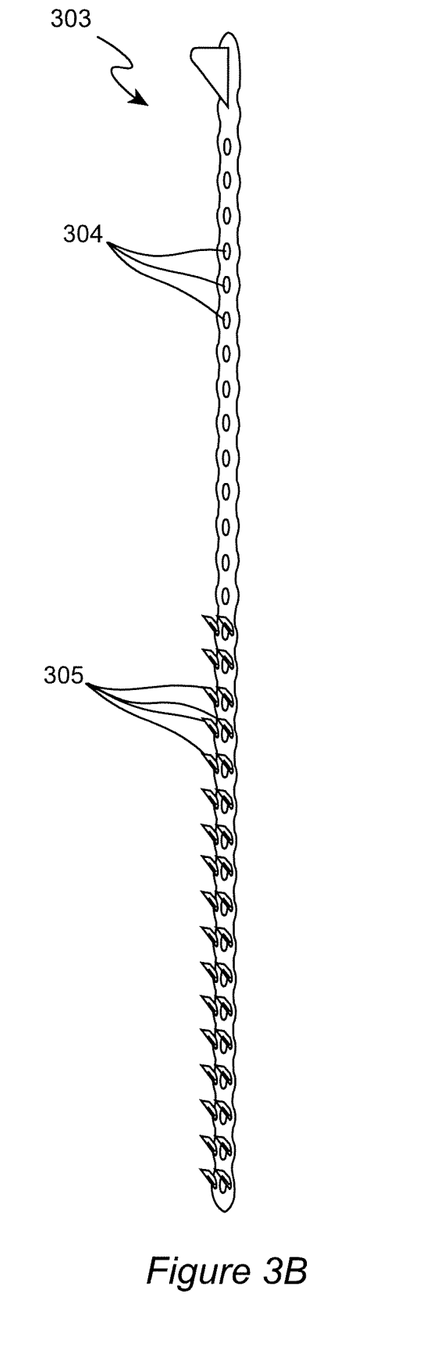

FIGS. 3A and 3B show example implantable fixation devices 301 and 303 with a ribbon configuration, meaning the overall shape is that of a ribbon, strip, or band, for example. Both devices 301 and 303 include at least one series (e.g., row) of suture holes 304 and a plurality of rows of tines 305. Alternative configurations may include two or more series of suture holes and additional rows of tines. According to an exemplary breast reconstruction surgery employing, for example, implantable fixation device 301 or 303, a surgeon places one or more sutures (e.g., 2-3 sutures) through the platform holes 304 to anchor the device to the tissue sling. Just one set of example dimensions for an implantable fixation device 301 or 303 is 15.5 cm length, 5 mm width, and 0.25 mm platform thickness. The example implantable fixation devices 301 and 303 have 17 rows of two tines for a total of 34 tines each. Tine height is 2.5 mm, and the tines are positioned at a 45° angle with respect to the backing. Alternative configurations may be of a different width (e.g., less than or equal to 7 mm, less than or equal to 6 mm, less than or equal to 5 mm, less than or equal to 4 mm), different length (e.g., less than or equal to 10 cm, less than or equal to 7 cm, less than or equal to 5 cm), or of a different geometry such as triangular or rectangular. The spacing of the holes 304 may also be such that the holes match the arc created when the suture needle is rotating from entry to exit on the tissue sling. Generally, implantable fixation device length may range from several centimeters (e.g., 4 cm) up to 15 cm. Tine count on a single backing (in particular, tine count for tines which contact or imbed in underlying surfaces of the overlying skin flap) may be as high as 68-100, for example. The tine count is generally dependent on the width and length of the implantable fixation device. Implantable fixation devices according to the invention may also have platforms that are thicker or thinner than the example devices 301 and 303. A device's platform may also be of variable thickness with, for example, thicker zones where the suture is ultimately in direct contact with the backing. The edges of holes 304 and/or other edges of implantable fixation devices may be rounded to reduce the possibility of damaging or cutting the suture or of the suture damaging the device. It should be appreciated that these specific geometric dimensions, configurations, and tine counts are provided by way of example and are not intended to limit the invention beyond what is explicitly recited in the appended claims. The preferred size and tine count varies depending on the size of the skin flap and the placement of the device(s) (see, e.g., FIGS. 4A-4H). The implantable fixation device 301 includes tines along an entirety of the length of the ribbon shaped platform. The implantable fixation device 303, as one possible alternative, includes tines only for a portion of the entirety of the length of the ribbon shaped backing. The non-tine backing portion may be employed to anchor the device 303 more superiorly to the pectoralis muscle above the tissue sling to provide additional anchoring strength in a more vertical or lateral-vertical vector.

Figure 4A:
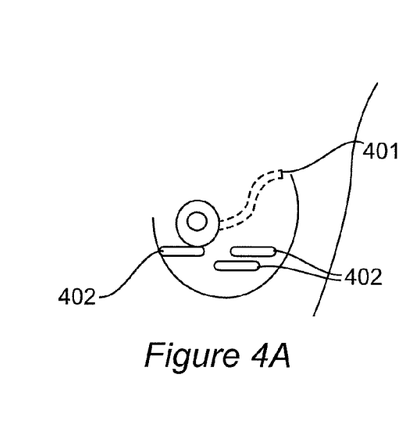
FIGS. 4A-4H show example incisions used in breast reconstruction and implantable fixation device orientations with respect thereto.
Figure 4B:
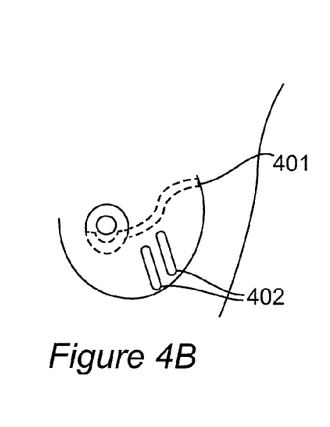
Figure 4C:
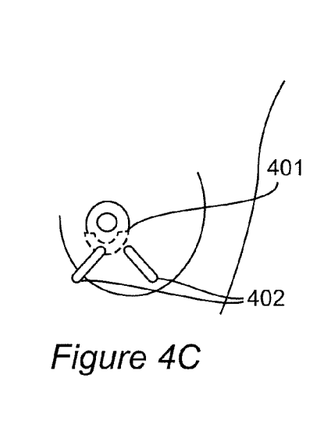
Figure 4D:
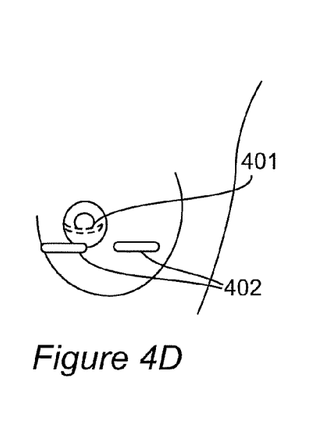
Figure 4E:
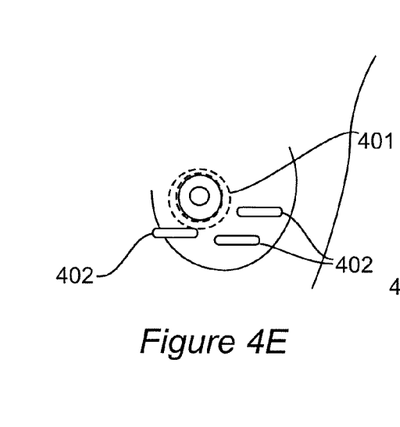
Figure 4F:
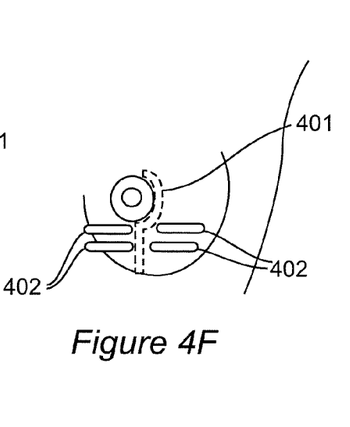
Figure 4G:
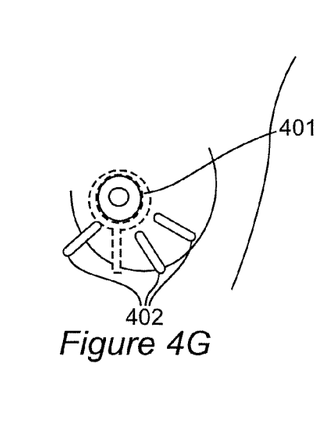
Figure 4H:
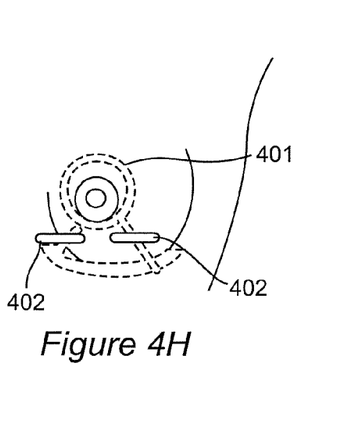

As yet further variations, implantable fixation devices with opposing tine orientations (see, e.g., FIGS. 11A and 11B) may be used in the case of vertical incisions (see, e.g., FIGS. 4F, 4G, and 4H). In this case, tines are angled towards the center of the device, allowing fixation towards the incision on both sides of the incision. This configuration stabilizes movement of the skin flap while also reducing tension at the incision. Tight, constricting suture in a thin skin flap can reduce blood flow and cause tissue necrosis.

Figure 3C:
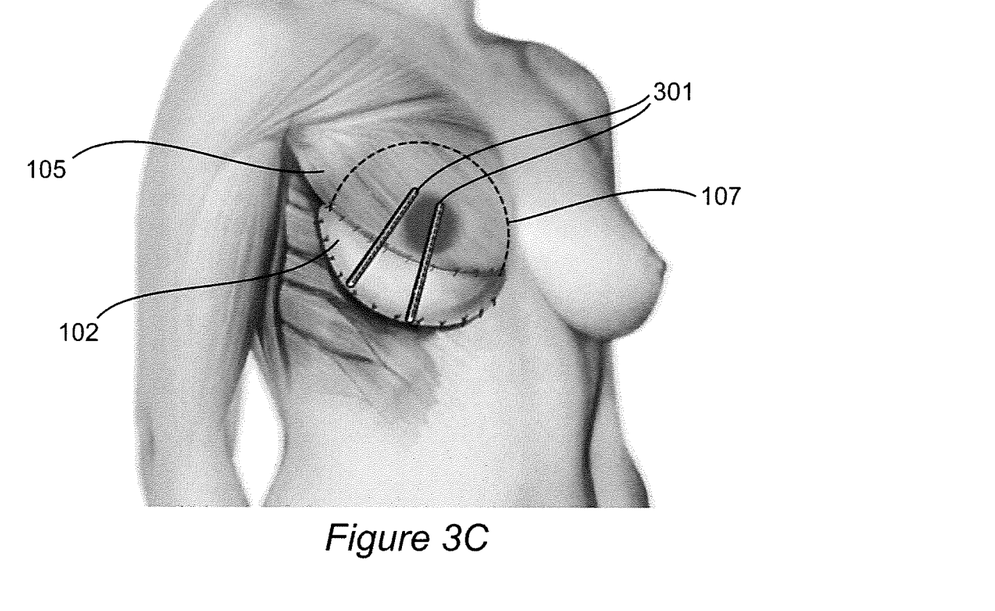
FIGS. 3C and 3D show implantable fixation devices according to FIG. 3A as arranged after breast reconstruction surgeries.
Figure 3D:
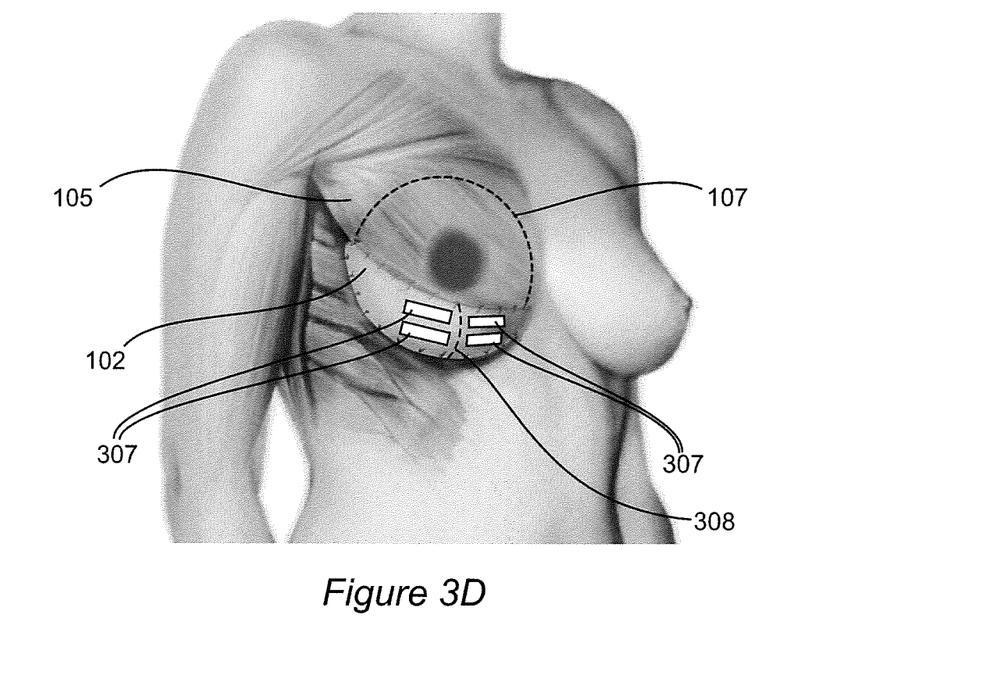

A variety of geometric sizes for implantable fixation devices are provided based on different incision locations and patterns on the breast. As used herein, a singular "implantable fixation device" does not necessarily have a single backing, although many embodiments do in fact have a single backing. In FIG. 3C, the implantable fixation device 301 includes two backings with ribbon geometry. It is also accurate to describe FIG. 3C as having two implantable fixation devices 301, each with a single backing. FIG. 3D shows the use of implantable fixation device(s) 307 comprising four ribbon shaped backings collectively providing lateral and medial stabilization of the skin flap to the tissue sling. The device(s) 307 are arranged to either side of a vertical incision 308 and are 7.5 cm in length. Alternatively, the length may be less than or equal to 7 cm, e.g., for smaller breasts. Depending on the location of skin incision(s), one, two, three, or more ribbon implantable fixation devices may be used for a single breast reconstruction, for example. The individual backings may furthermore have their own configurations of tacks/tines and/or suture holes. When suture is used, it is preferable that an instrument such as a ribbon malleable retractor or wide forcep is inserted laterally under the tissue sling. The underlying instrument then protects the tissue expander from possible puncture from the suture's needle. Once multiple suture has been placed though the sling 102 (e.g, the non-autologous tissue graft) and the implantable fixation device via the numerous suture holes present in the backing, the device would be fixed and stable with respect to the overlying skin flap.

FIGS. 4A-4H show a variety of common incisions 401 used in breast reconstruction and exemplary implantable fixation device placement with respect thereto. The implantable fixation devices, though they may differ in length or other parameters as described herein, are generally identified as 402 in FIGS. 4A-4H.

Figure 5A:
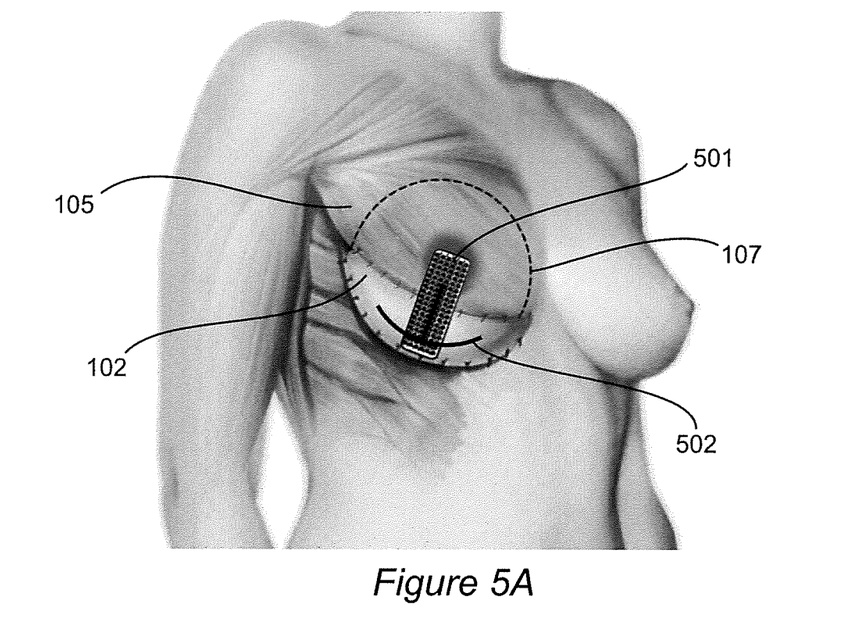
FIGS. 5A and 5B show example embodiments of an implantable fixation device used in breast reconstruction surgery with variations in platform size, shape, and tine configurations.
Figure 5B:
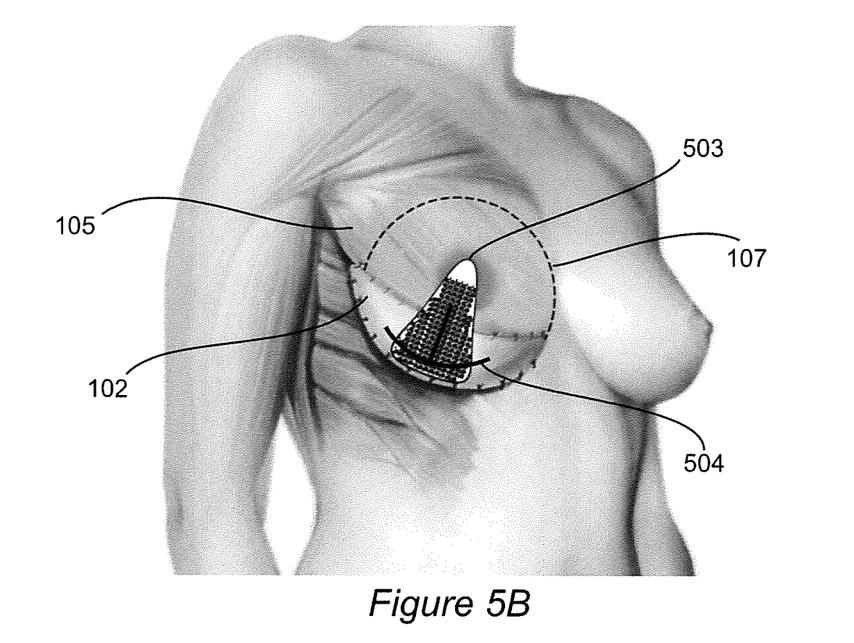

FIG. 5A shows an implantable fixation device 501 having a rectangular geometry. FIG. 5B shows an implantable fixation device 503 having a triangular geometry. A Wise incision pattern 502/504 (after closure) is shown superimposed on the breasts in both FIGS. 5A and 5B. The illustrated devices 501 and 503 may also be used with other incision patterns and locations. Alternative geometries include but are not limited to oval and round shapes.

Benefits of devices and methods according to the teachings herein include an enhanced cosmetic result of the breast reconstruction surgery. The implantable fixation devices (e.g., 101, 301, 303, 307, 402, 501, and 503) off-load tension on the overlying skin due to an anchored position under the overlying skin flap. By providing substantial lift of the skin flap from an underside thereof, less tension is required to close the incision(s). Additional benefits include a more rapid integration of the overlying skin flap to the implanted tissue sling (e.g., non-autologous tissue graft). This reduces drain time. The implantable fixation devices reduce seroma formation due to the added stability of the skin flap to the tissue sling. Referring again to FIG. 1, the implantable fixation device 101 effectively eliminates movement (e.g., sliding) between the flap of overlying skin 103 and the tissue sling 102. Flap stabilization facilitates tissue integration of non-autologous tissue with the patient's own tissue.

Figure 6A:
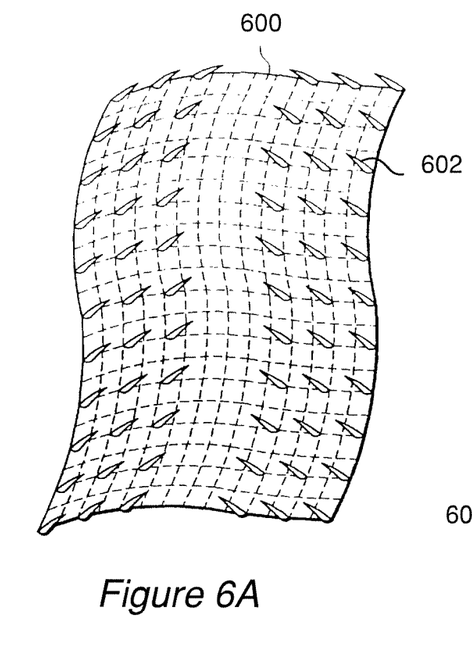
FIGS. 6A-6D are plan, perspective views of various implantable fixation devices.
Figure 6B:
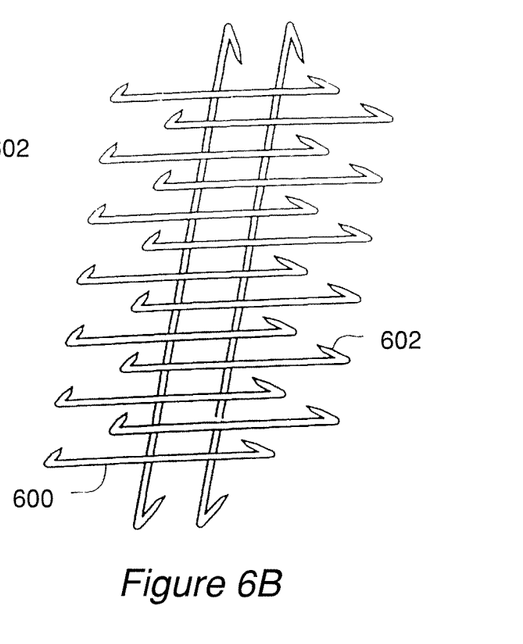
Figures 6C, 6D:
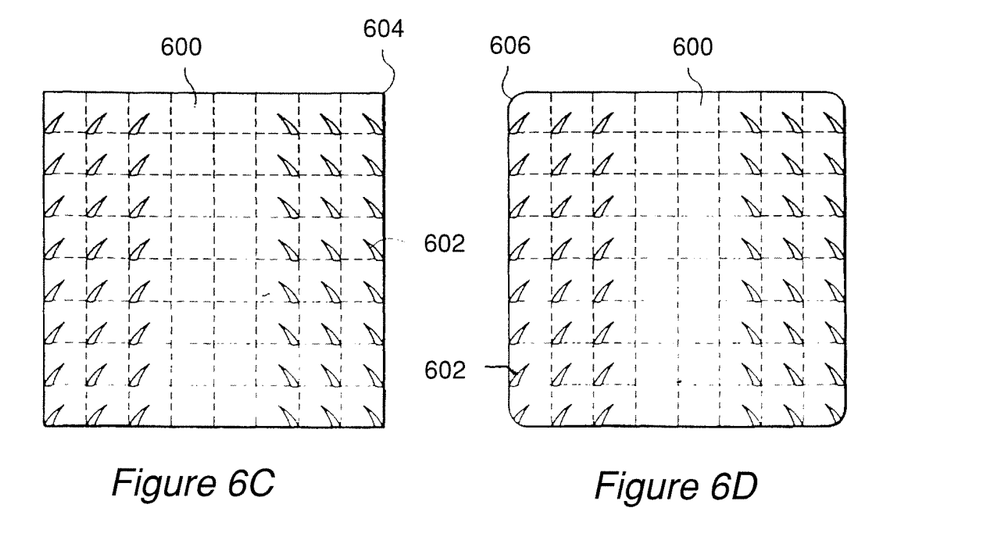
Figure 7A:
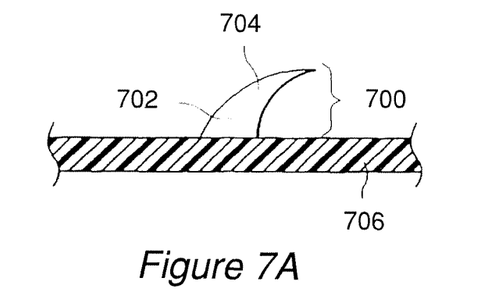
FIGS. 7A-7E are side views of various attachment point shapes and orientations.
Figure 7B:
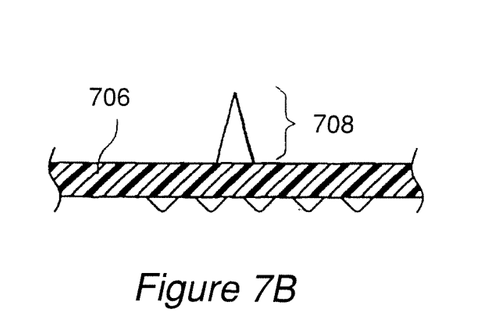
Figure 7C:
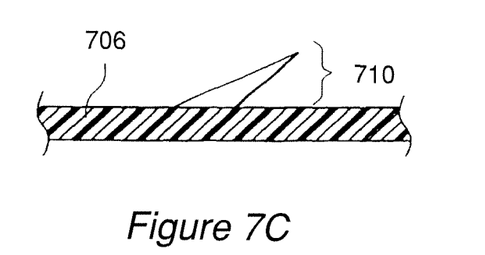
Figure 7D:
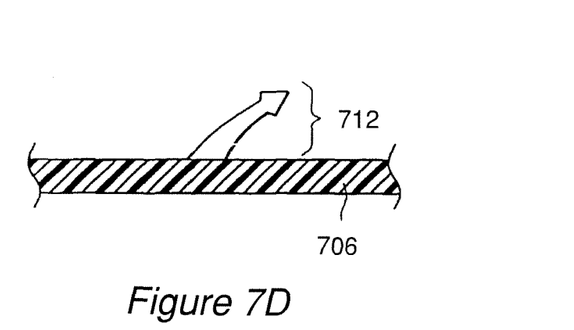
Figure 7E:
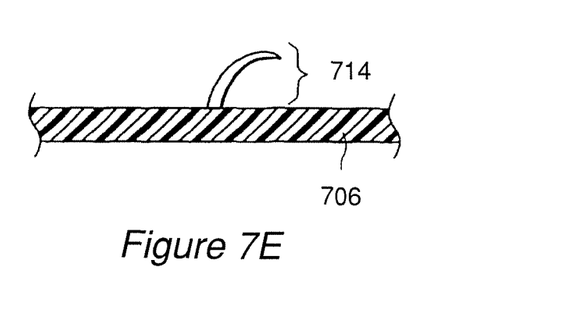

The implantable fixation device 101 is of the general configurations shown in FIGS. 6A-6B and comprises a plurality of attachment points 602 emanating from a supportive backing 600 that is a generally a porous material that may have the structure of a mesh, net, or lattice. The degree of flexibility of the backing is determined by the material of construction, the shape, and dimensions of the device. Also, depending on the type of material used, the thickness of the backing as well as its width and length may determine the flexibility of the device. Furthermore, the backing may be pre-fabricated into different shapes as shown by the sharp corners 604 and rounded corners 606 in FIGS. 6C and 6D. The fabricated cross-sectional shape and dimensions of the mesh elements may vary to promote flexibility in regions of the backing. The cross-sectional shape of the mesh elements may be chosen to minimize local compressive stress between the backing and surface it rests upon, or have rounded and filleted edges to be less obtrusive to local circulation. The plurality of attachment points distributes tension over the contact area between the device and the tissue.

Materials such as biodegradable polymers are preferably used to construct the backing and attachment points. Polymers synthesized from monomers comprising esters, anhydrides, orthoesters, and amides are particularly suitable for biodegradation. Examples of biodegradable polymers are polyglycolide, polylactide, poly-α-caprolactone, polydiaxanone, polyglyconate, polylactide-co-glycolide, and block and random copolymers of these polymers. Copolymers of glycolic, lactic, and other α-hydroxy acids are highly desirable. Although it is generally preferred to use a single polymer or copolymer in a specific device, generally for ease of construction, the invention is not so limited. For example, according to one example embodiment, two or more types of polymers or copolymers (or molecular weights of the same polymer or copolymer) may be used together. For instance, the backing material might be produced from a more flexible polymer and the points or tines of a stiffer material. The inflammatory response to these polymers is minimal, and they have been safely used in suture materials, stents, drug delivery devices, orthopedic fixation devices, and intestinal anastomotic rings.

Generally, "attachment points" can be used interchangeably herein with "tines" or "prongs". These tines will refer both to points which are either sharp (i.e., able to separate tissue in a chosen use) or blunt (i.e., not able to separate tissue in that use). The attachment points may also be referred to as "barbs" when those points have the retaining point shown in several of the Figures discussed below.

Figure 8A:
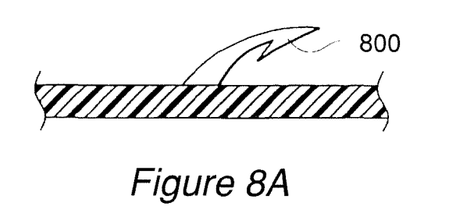
FIGS. 8A-8D and 8F-8G are side views of various attachment points.
Figure 8B:
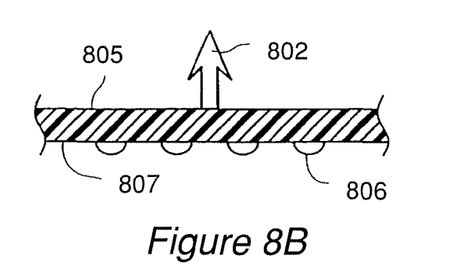
Figure 8C:
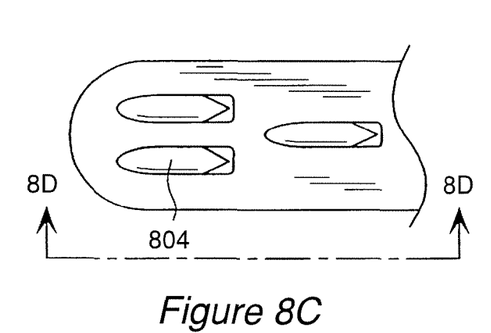
Figure 8D:
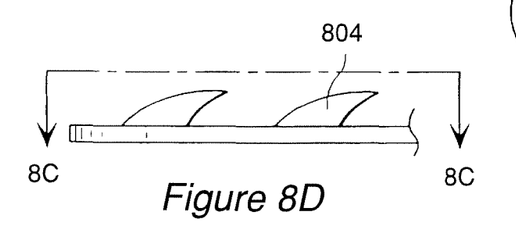

As shown in FIGS. 7A-7E, the shape of the attachment points or barbs may be varied. The tines may be canted or erect, but in a preferred variation, the general structure of the tines is of a rose thorn shape. The tines 700 have a wide base 702 that supports a projection 704 from the backing 706 against the degree of tension required to close a wound or approximate tissue. For example, the attachment points may be erect tine (FIG. 7B-708), canted tine (FIG. 7C-710), canted arrowhead (FIG. 7D-712), canted hook (FIG. 7E-714), or may have a single straight cross-section (FIG. 8G-811) that is nail-like, that does not vary over the length of the prong, for example, similar in shape to a nail or sharpened pencil. Furthermore, the tip of the attachment points may be varied as shown in FIGS. 8A-8D. The tips may be barbed 800, arrowhead (double-barb) 802, or cheese grater 804. A side view of the cheese grater tips is shown in FIG. 8D.

The connection of the prong to the backing may be rounded or filleted, or the backing built-up around the prong, to reduce structural stress concentrations. The backing or connecting structure may branch out away from the center, with each branch in turn branching to grapple tissue in a distributed fashion. All edges of the device may be smooth except where sharpness is needed at the tip of the prong to pierce into the tissue. Once the prongs pierce into the tissue, the tissue may become supported against the backing to minimize additional piercing or irritation by the prong tip. The device may be molded, stamped, machined, woven, bent, welded or otherwise fabricated to create the desired features and functional properties.

Figure 8E:
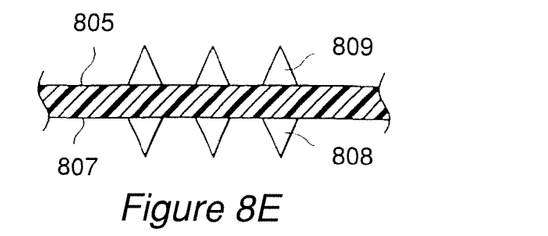
FIG. 8E is a side view of a two-sided implantable fixation device.
Figure 8F:
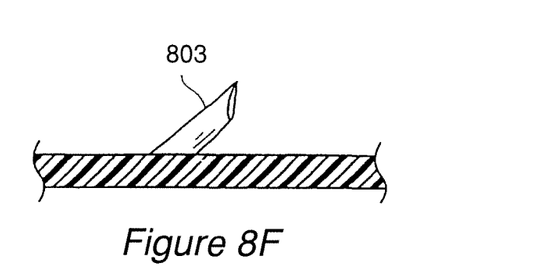
Figure 8G:
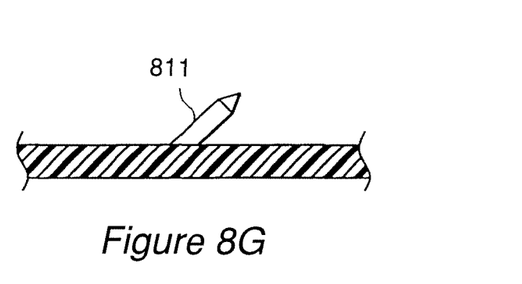
Figure 8H:
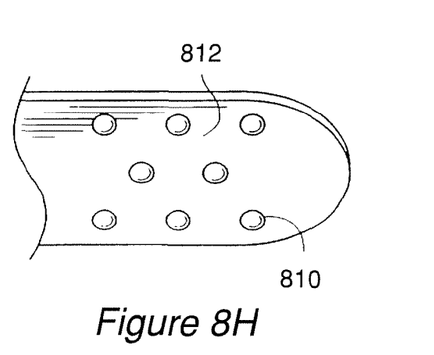
FIG. 8H is a plan, reverse perspective view of nubs on the inferior surface of an implantable fixation device.

According to some exemplary embodiments including that which is shown in FIG. 1, an implantable fixation device 101 has attachment points both on a front side and a back side. As shown in FIGS. 8B and 8E, the front side 805 and back side 807 have attachment points. The attachment points 809 on the front side 805 correspond to the tines 111 in FIG. 1. They are imbedded in the subcutaneous tissue 104 of the tissue flap 103 and approximate the tissue at the incisions. The attachment points 808 on the back side 807 correspond with the tines 109 which make contact with or imbed within the muscle 105 or sling 102. According to an example embodiment, tines 109 may be configured as round nubs 806 or pointed nubs 808 as shown in FIGS. 8B and 8E. Soft tissue of the breast may be gently pressed into open regions of the backing which helps to fix the implantable fixation device in place against both underlying and overlying tissue. FIG. 8H shows a reverse view of the nubs 810 on the back side of the device 812. The attachment points on a two-sided device are not limited to the combinations disclosed above, but may comprise any combination of the previously mentioned attachment point shapes and orientations.

Figure 9A:
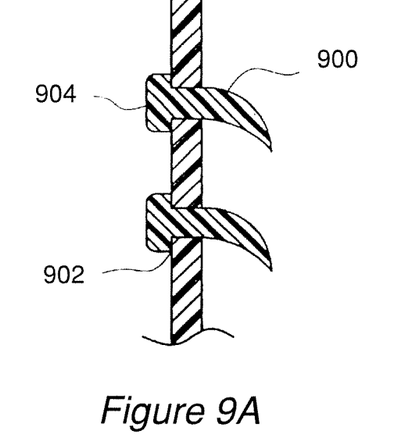
FIG. 9A is a side, cross-sectional view of attachment points that run through the width of a backing.
Figure 9B:
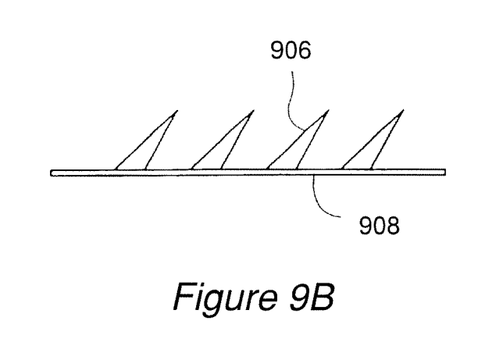
FIG. 9B is a side view of attachment points on a strip of backing material.
Figure 9C:
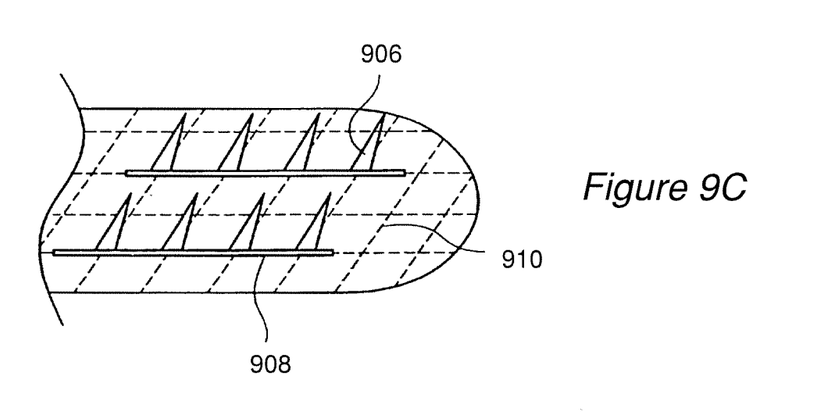
FIG. 9C is a plan, perspective view of the embodiment in 9B on a backing.
Figure 9D:
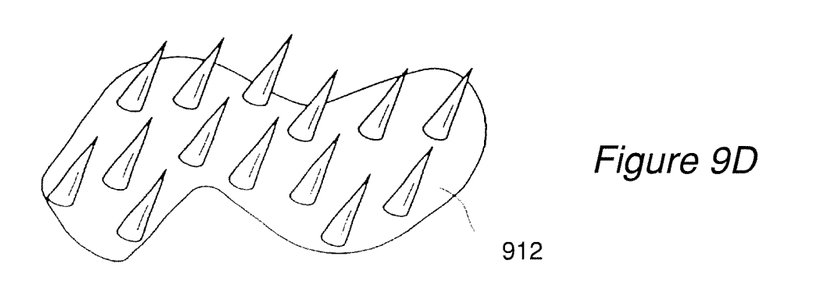
FIG. 9D is a plan, perspective view of attachment points on a solid backing.

Structural variations can also be made to the backing of the device. As shown in FIG. 9A, the attachment points 900 may be placed through a plurality of openings in the backing 902 and secured to the backing by a flange 904 or hub. In FIGS. 9B and 9C, the points 906 may also connect to strips 908 of the same material as the attachment points which are then secured to a backing 910. The backing may also be comprised of a solid material 912 instead of a porous material.

The extent of porosity or total surface area used to control the absorption rate of the device may also be used to optimize the strength-to-mass properties of the device, increasing the section modulus of structural cross-sections per unit mass. The backing structure may comprise partial folds, waves, or grooves to help hold tissue against both surfaces of the backing. Regions of the backing may function as suction cups to help hold tissue to the backing.

Figure 10A:
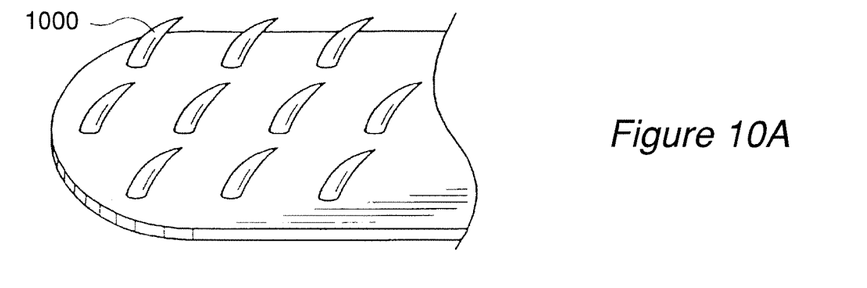
FIG. 10A is a plan, perspective view of attachment points canted in one direction.
Figure 10B:
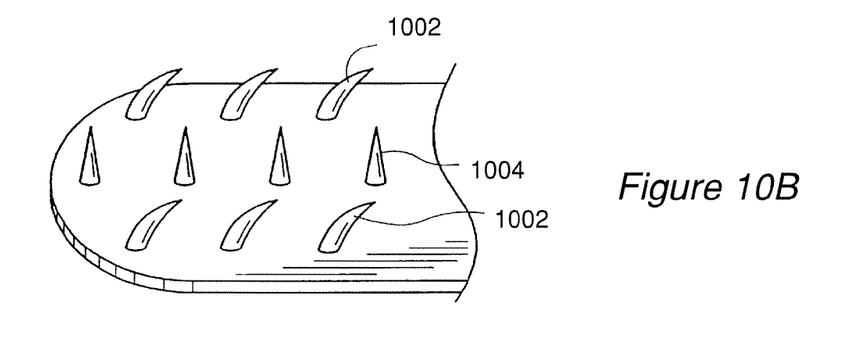
FIGS. 10B-10D are plan, perspective views of attachment points with various orientations on a backing.
Figure 10C:
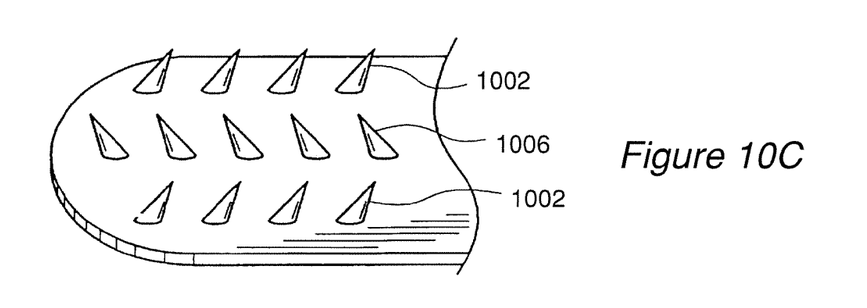
Figure 10D:
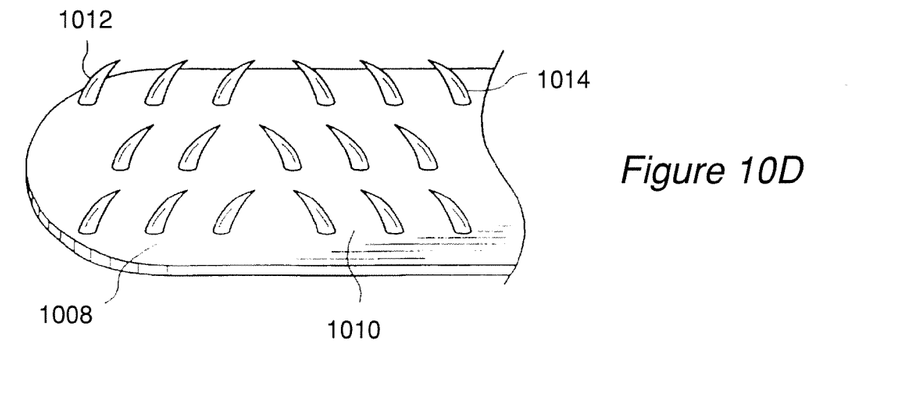

The density, distribution, length, and orientation of attachment points on the backing may be modified. Attachment points may be bent or curve gradually, with the tip directed at an optimal angle relative to the backing to aid device penetration and stability within the tissue, and to reduce tissue irritation after device installation. Attachment points may be canted in one direction 1000, such as toward the center of the device as shown in FIG. 10A. The attachment points may also be variously oriented, such as toward center 1002 and erect 1004, or toward center 1002 and away from center 1006. It is within the scope of this invention to have attachment points extending in any relative direction or orientation on the backing. Or, as shown in FIG. 10D, the backing is divided into a first area 1008 and a second area 1010. Attachment points in the first area 1012 and second area 1014 are canted toward each other. The inventive device may also be sectioned into a plurality of areas, with each section being variously oriented to another section.

Figure 10E:
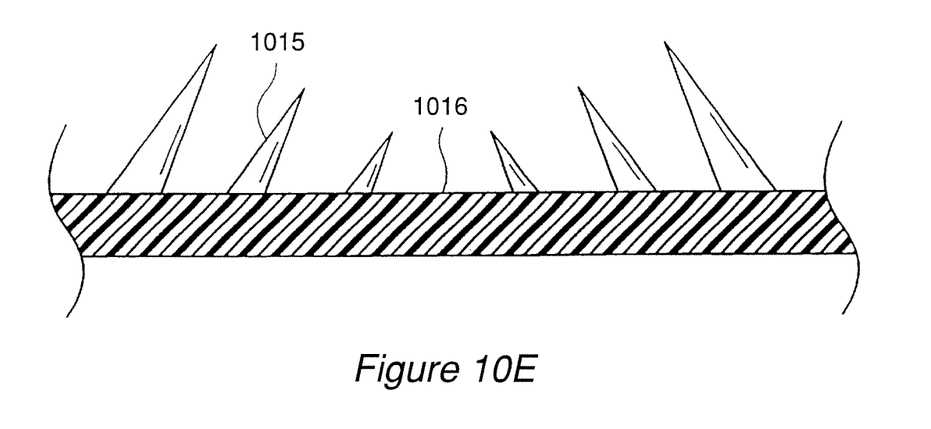
FIG. 10E is a side view of attachment points becoming progressively shorter the closer they are to the center of the device.
Figure 10F:
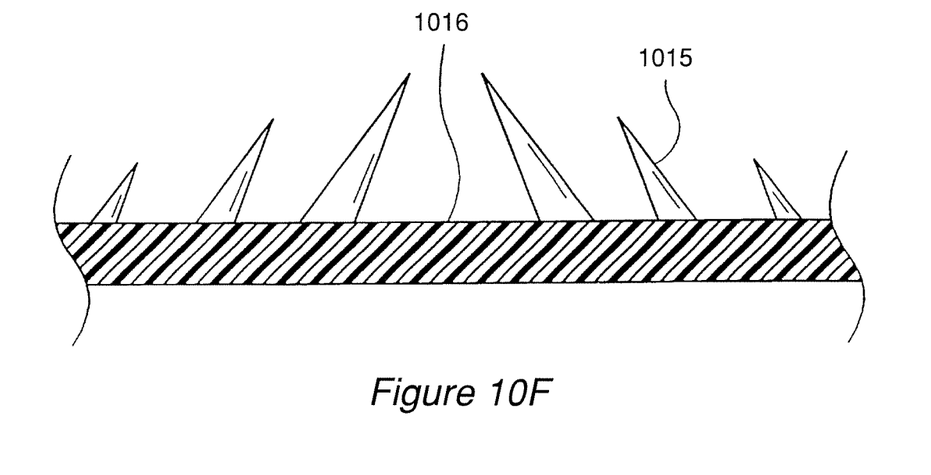
FIG. 10F is a side view of attachment points becoming progressively shorter the farther they are from the center of the device.

In another variation of the invention, attachment points of various lengths emanate from a single backing. For example, in FIG. 10E, the attachment points 1015 are progressively shorter the closer they are to the center of the device 1016. The attachment points 1015 may also become progressively shorter the farther they are from the center of the device as shown in FIG. 10F. The variations shown in FIGS. 10B and 10C have regions of attachment points canted toward the center 1002 and with other regions of attachment points with erect points (1004 in FIG. 10B) or canted away from the other end (1006 in FIG. 10C) of the device. These variations are more difficult to dislodge by to-and-fro movement or during placement of the device.

Figure 11A:
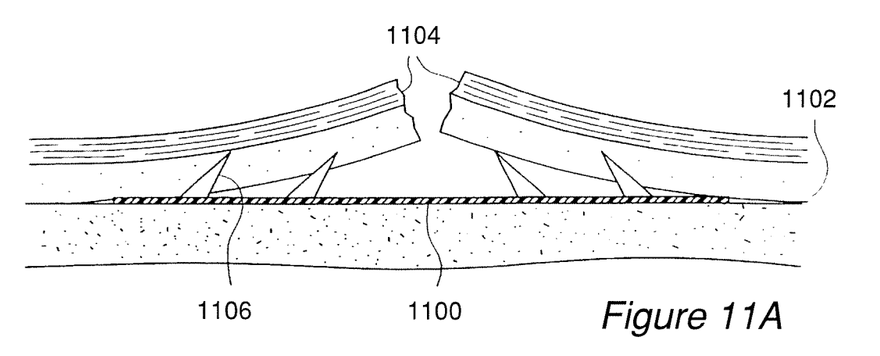
FIGS. 11A-11B are schematic views of a skin wound and wound repair using the implantable fixation device.
Figure 11B:
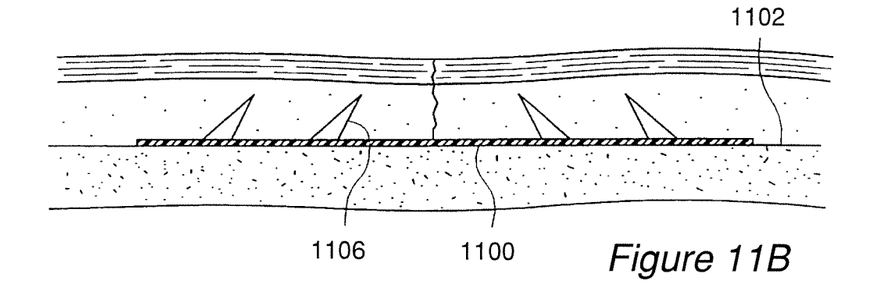

Portions of simple wound closures are shown in FIGS. 11A-11B. These wound closures involve placing the implantable fixation device 1100 at the bottom of the wound, usually at the level of the sub-dermis 1102. The edges of the wound 1104 are approximated and then secured by fixation, e.g., by pressing, to the multiple attachment points 1106.

While the invention has been described in teens of exemplary and preferred embodiments and features, it should be understood that these are non-limiting examples, and features described with respect to one embodiment may generally be included with other embodiments explicitly discussed herein as well as embodiments not explicitly discussed but arrived by those of skill in the art at based on the disclosed teachings. The invention is not limited by the examples, and variations may be performed in the practice of the invention within the spirit and scope of the appended claims.

What we claim is:

1. A surgical method for breast reconstruction surgery, comprising steps of:
    securing in a breast reconstruction patient a tissue sling configured to support a tissue expander or breast implant, the tissue sling comprising non-autologous soft tissue including one or more of acellular dermis, acellular bovine pericardium, porcine acellular dermis, and a cadaveric tissue graft;
    fixing an implantable fixation device which includes a platform fixable to tissues with at least a plurality of tines to both the tissue sling and muscle tissue of the patient; and
    closing overlying skin such that outward projecting tines of the plurality of tines contact or imbed in an undersurface of the overlying skin.

2. The surgical method of claim 1, further comprising a step of selecting the implantable fixation device according to one or more of a platform size, shape, porosity, flexibility, material composition, and tine configuration such that, after the steps of fixing and closing, the implantable fixation device stabilizes the tissue sling with respect to the overlying skin.

3. The surgical method of claim 1, further comprising a step of orienting the implantable fixation device along one or more vectors of lift to stabilize one or more of the tissue sling and pectoralis muscle tissue with respect to the overlying skin.

4. A surgical method for breast reconstruction surgery, comprising steps of:
   securing in a breast reconstruction patient a tissue sling configured to support a tissue expander or breast implant, the tissue sling comprising soft tissue;
   orienting an implantable fixation device along one or more vectors of lift to stabilize one or more of the tissue sling and pectoralis muscle tissue with respect to overlying skin;
   fixing the implantable fixation device which includes a platform fixable to tissues with at least a plurality of tines to both the tissue sling and muscle tissue of the patient; and
   closing the overlying skin such that outward projecting tines of the plurality of tines contact or imbed in an undersurface of the overlying skin.

5. The surgical method of claim 4, further comprising a step of selecting the implantable fixation device according to a platform size, shape, porosity, flexibility, material composition, and tine configuration such that, after the steps of fixing and closing, the implantable fixation device stabilizes the tissue sling with respect to the overlying skin.

\* \* \* \* \*